United States Patent [19]

Morganson et al.

[11] 4,436,947

[45] Mar. 13, 1984

[54] OLEFIN OLIGOMERIZATION USING BORON TRIFLUORIDE AND A THREE-COMPONENT COCATALYST

[75] Inventors: Neal E. Morganson, McCandless Township, Allegheny County; Adam V. Vayda, Oakmont, both of Pa.

[73] Assignee: Gulf Research & Development Company, Pittsburgh, Pa.

[21] Appl. No.: 301,446

[22] Filed: Sep. 11, 1981

[51] Int. Cl.$^3$ .............................................. C07C 3/18
[52] U.S. Cl. .................................... 585/525; 585/510
[58] Field of Search ............................... 585/525, 510

[56] References Cited

U.S. PATENT DOCUMENTS 4,045,507 8/1977 Cupples et al. ...................... 585/517

*Primary Examiner*—Curtis R. Davis
*Attorney, Agent, or Firm*—Deane E. Keith; Forrest D. Stine; Donald L. Rose

[57] ABSTRACT

Olefin oligomers suitable as lubricants are prepared with a catalyst comprising boron trifluoride and a mixture of an alcohol, a polyol and a ketone. 1-Decene is oligomerized to a liquid product having a high trimer to tetramer ratio using boron trifluoride and a mixture of n-butanol, ethylene glycol and methylethyl ketone.

8 Claims, No Drawings

OLEFIN OLIGOMERIZATION USING BORON TRIFLUORIDE AND A THREE-COMPONENT COCATALYST

SUMMARY OF THE INVENTION

Olefins are oligomerized using a four-component catalyst combination comprising boron trifluoride and a mixture of an alcohol, a polyol and a ketone. When 1-decene is oligomerized using boron trifluoride and a liquid mixture of n-butanol, ethylene glycol and methylethyl ketone, the resulting liquid oligomer is produced in good yield with a high trimer to tetramer ratio.

DESCRIPTION OF THE INVENTION

Oligomers of certain 1-olefins are highly useful in preparing functional fluids such as lubricants, hydraulic fluids, transmission fluids, transformer fluids, and the like, generally compounded with other functional fluid components including appropriate additives. Each functional fluid product and generally the base fluid from which it is prepared must conform with established viscosity and volatility specifications. These alpha-olefin oligomer products are generally prepared by the cationic polymerization of the 1-olefin using a Friedel-Crafts catalyst, preferably boron trifluoride. The oligomer product is then hydrogenated in a conventional manner to stabilize the oligomer against oxidation and degradation.

In recent years 1-decene oligomer mixtures have been widely used in engine lubricant and hydraulic fluid formulations. Using conventional reaction conditions, the 1-decene polymerization reaction prepares a mixture of the oligomers including the dimer, trimer, tetramer, and pentamer comprising branched-chain molecular structures in which the branches are of relatively long carbon length. The dimer is removed for separate use to avoid volatilization loss from functional fluids comprising the higher oligomers. Minor amounts of oligomers higher than the pentamer, such as the hexamer, may be present but since their analysis and separation from the pentamer is difficult, they, if present, are generally reported as pentamer.

The composition of the oligomer mixture that is obtained from the oligomerization reaction is generally too rich in the tetramer and pentamer fractions to meet the viscosity specifications for desired formulations. This usually requires the separation of the oligomer composition into one or more product fractions comprising the trimer or a mixture of oligomers, rich or predominating in the trimer, depending on the particular need. And most significantly, this generally results in a significant unusable surplus of the higher oligomer fractions to be discarded, namely, the tetramer and pentamer fractions, as reported in U.S. Pat. No. 3,997,627. As a result those working in this field have directed their efforts towards increasing the selectivity of the 1-decene oligomerization reaction to the trimer, often referred to as improving the trimer to tetramer ratio or the ratio of the trimer to the heavier fractions.

The catalyst generally recommended for the oligomerization of 1-olefins is boron trifluoride and a liquid cocatalyst. The boron trifluoride must be present in molar excess of the cocatalyst for optimum results. A variety of substances have been used or suggested for use as the cocatalyst including water, various alcohols, ethers, polyols, aliphatic carboxylic acids, anhydrides, esters, and ketones, all of which are specified for this use in U.S. Pat. No. 4,045,507.

We have discovered that the combination of boron trifluoride catalyst together with a mixture of certain cocatalyst substances, and more specifically a mixture of an alcohol, a polyol and a ketone, beneficially affects the oligomerization reaction and also benefits the resulting oligomer product. For example, when 1-decene is oligomerized using boron trifluoride, and this three-component cocatalyst combination, both the conversion and the trimer to tetramer ratio are improved.

The alcohol which is suitable in our cocatalyst mixture is an aliphatic alcohol having from one to about ten carbon atoms or a mixture thereof, preferably from about two to about four carbon atoms. This alcohol is used in the amount of about 50 to about 98 weight percent, preferably about 75 to about 95 percent of the total cocatalyst combination. Suitable alcohols include methanol, ethanol, propanol, isobutanol, n-decanol and the like. The preferred alcohols are the two to four carbon alcohols, and the most preferred alcohol is n-butanol.

The polyol which is used in our cocatalyst combination is selected from ethylene glycol, propylene glycol, butane diol, glycerine, and the like. A two or three carbon diol is preferred. The polyol or mixture of polyols are present in the amount of about one to about 25 weight percent, preferably about two to about 15 percent of the total cocatalyst combination. The ketone which is used is selected from aliphatic ketones having from three to about ten carbon atoms and mixtures thereof, or preferably ketones having three or four carbon atoms such as acetone, methylethyl ketone, methyl n-butyl ketone, and the like. The ketone is also present broadly in the range between about one and about 25 weight percent, preferably within the range of about two to about 15 percent.

The cocatalyst mixture can be used in a catalytic amount such as from about 0.01 to about 3.0 weight percent of the olefin undergoing oligomerization, preferably from about 0.1 to about 1.0 weight percent.

The oligomerization reaction is carried out using the four-component catalyst described herein and using conventional reaction conditions and procedures. Thus, the oligomerization can be carried out as a batch reaction as described in U.S. Pat. No. 3,780,128 or it can be carried out as a continuous reaction such as described in U.S. Pat. No. 4,045,507. Other types of oligomerization reactors and reaction systems are also suitable for use with our novel catalyst system. In general, any equipment or production layout designed for oligomerization with boron trifluoride catalyst can be used with our catalyst.

The oligomerization reaction is conducted within the temperature range of between about −20° C. to about 90° C. with a temperature within the range of between about 20° C. and about 70° C. being preferred. The partial pressure of boron trifluoride in the oligomerization reactor is broadly maintained within the range of between about five and about 500 psig or higher, with a range of between about 20 and about 100 psig being preferred.

The olefins which can suitably be oligomerized by the novel catalyst described herein have between about six and about 20 carbon atoms, preferably between about 10 and about 14 carbon atoms. The olefins can be straight-chain or branched-chain olefins and can be alpha-olefins or internal olefins. The preferred olefins are normal alpha-olefins. When olefins having more than 13 carbon atoms are oligomerized, the dimer may be the preferred oligomer fraction.

DESCRIPTION OF PREFERRED EMBODIMENTS

EXAMPLES 1-5

1-Decene was oligomerized in a series of experiments using boron trifluoride and a cocatalyst mixture comprising n-butanol, methylethyl ketone and ethylene glycol. These experiments were carried out at steady state conditions by the continuous process described in U.S. Pat. No. 4,045,507 using two stirred tank reactors in series. The operating conditions and product analyses are set out in Table I.

TABLE I

| Example | 1 | 2 | 3 | 4 | 5 |
|---|---|---|---|---|---|
| Cocatalyst, wt % | | | | | |
| n-butanol | 100 | 91.4 | 91.4 | 91.4 | 80 |
| me. eth. ketone | 0 | 5.8 | 5.8 | 5.8 | 10 |
| eth. glycol | 0 | 2.8 | 2.8 | 2.8 | 10 |
| Cocat. conc., wt % | 0.56 | 0.66 | 0.80 | 0.36 | 0.40 |
| $BF_3$, conc., wt % | 0.63 | 0.79 | 0.81 | 0.55 | 0.65 |
| Temperature, °C. | 49–52 | 49–50 | 53 | 51–52 | 48–51 |
| Pressure, psi | 20 | 20 | 20 | 31–32 | 30 |
| Product, wt % | | | | | |
| $C_{10}$ | 10.0 | 7.3 | 9.3 | 7.7 | 5.5 |
| $C_{20}$ | 7.8 | 10.6 | 11.4 | 11.9 | 15.0 |
| $C_{30}$ | 50.1 | 58.3 | 58.3 | 55.4 | 55.5 |
| $C_{40}$ | 25.2 | 19.9 | 17.8 | 19.4 | 20.2 |
| $C_{50}$ | 6.9 | 3.9 | 3.2 | 5.6 | 3.8 |
| $C_{30}/C_{40+}$ | 1.56 | 2.45 | 2.78 | 2.22 | 2.31 |

It is noted from Table I that both the conversion and the trimer to tetramer and higher ratio is improved in all instances where the novel four-component catalyst combination was used.

The monomer and dimer were removed from each of the products from Examples 1 and 3. Each of the remainder portions was distilled into a trimer-rich fraction having a 210° F. viscosity of about 4 cSt and a tetramer-rich fraction having a 210° F. viscosity of about 6 cSt. The weight ratio of the 4 cSt fraction to the 6 cSt fraction resulting from Example 1 was 1.7:1, while the ratio of these fractions resulting from Example 3 was 3.3:1.

EXAMPLES 6-7

Two more experiments were carried out in the reactor system used in the preceding examples. 1-Decene was oligomerized using boron trifluoride catalyst at a concentration of 0.67 wt % and a n-butanol concentration of 0.58 in Example 6. In Example 7 the catalyst concentration was 0.73 weight percent boron trifluoride and 0.64 percent of a cocatalyst mixture consisting of about six percent methylethyl ketone, three percent ethylene glycol and the remainder n-butanol. The temperatures in the reactors were 41°–45° C. and the pressures were 19–22 psi. The products were separated into 4 cSt and 6 cSt fractions, as described in connection with Examples 1 and 3. The ratio (weight) of the 4 cSt fraction to the 6 cSt fraction produced in Example 6 using pure n-butanol as the cocatalyst was 1.3:1, while the ratio resulting from the use of the three-component cocatalyst was 3.1:1. The two fractions obtained using the three-component cocatalyst were analyzed and the viscosities (ASTM-D445) and viscosity indexes were determined. This information is set out in Table II.

TABLE II

| Fraction | 4 cSt | cSt |
|---|---|---|
| Composition, wt % | | |
| $C_{20}$ | 0.5 | — |
| $C_{30}$ | 79.3 | 26.6 |
| $C_{40}$ | 20.2 | 52.0 |
| $C_{50}$ | — | 21.4 |
| Viscosity, cSt | | |
| at −40° F. | 2,465 | 7,269 |
| at 0° F. | 334 | 813 |
| at 100° F. | 18.42 | 33.09 |
| at 210° F. | 3.98 | 5.95 |
| Viscosity Index | 125 | 138 |

It is to be understood that the above disclosure is by way of specific example and that numerous modifications and variations are available to those of ordinary skill in the art without departing from the true spirit and scope of the invention.

We claim:

1. A process for producing a mixture of olefin oligomers which comprises contacting an olefin having from about six to about 20 carbon atoms or a mixture thereof with a catalyst comprising boron trifluoride and a cocatalyst comprising between about 50 and about 98 weight percent of an aliphatic alcohol having from one to about ten carbon atoms, between about one and about 25 percent of an aliphatic ketone having from three to about ten carbon atoms and about one to about 25 percent of a polyol selected from ethylene glycol, propylene glycol, butane diol and glycerine.

2. A process for producing a mixture of olefin oligomers in accordance with claim 1 wherein the olefin is an alpha-olefin having between about ten and about 14 carbon atoms or a mixture thereof.

3. A process for producing a mixture of olefin oligomers in accordance with claim 1 wherein the partial pressure of the boron trifluoride is between about five and about 500 psig, the cocatalyst mixture comprises between about 0.01 and about 3.0 weight percent of said olefin, and the temperature is between about −20° C. and about 90° C.

4. A process for producing a mixture of olefin oligomers in accordance with claim 1 wherein the cocatalyst comprises between about 75 and about 95 percent of the aliphatic alcohol, between about two and about 15 percent of the aliphatic ketone and between about two and about 15 percent of the polyol.

5. A process for producing a mixture of olefin oligomers in accordance with claim 4 wherein the aliphatic alcohol contains from about two to about 4 carbon atoms, the ketone contains from three to about four carbon atoms and the polyol is ethylene glycol or propylene glycol.

6. A process for producing a mixture of olefin oligomers in accordance with claim 1 wherein the partial pressure of the boron trifluoride is between about 20 and about 100 psig, the cocatalyst mixture comprises between about 0.1 and about 1.0 weight percent of said olefin, and the temperature is between about 20° C. and about 70° C.

7. A process for producing a mixture of olefin oligomers in accordance with claim 1 wherein the olefin comprises 1-decene.

8. A process for producing a mixture of olefin oligomers in accordance with claim 4 wherein the alcohol is n-butanol.

* * * * *

UNITED STATES PATENT OFFICE
CERTIFICATE OF CORRECTION

Patent No. 4,436,947            Dated March 13, 1984

Inventor(s) Neal E. Morganson and Adam V. Vayda

It is certified that error appears in the above-identified patent and that said Letters Patent are hereby corrected as shown below:

Col. 4, line 2, the heading "cSt" should read -- 6 cSt --.

Signed and Sealed this

Thirtieth Day of April 1985

[SEAL]

Attest:

DONALD J. QUIGG

Attesting Officer      Acting Commissioner of Patents and Trademarks